(12) United States Patent
Wu et al.

(10) Patent No.: US 11,396,001 B2
(45) Date of Patent: Jul. 26, 2022

(54) HYBRID MICROCAPSULES

(71) Applicant: Firmenich SA, Geneva (CH)

(72) Inventors: Yongtao Wu, Shanghai (CN); Lahoussine Ouali, Geneva (CH)

(73) Assignee: Firmenich SA, Satigny (CH)

( * ) Notice: Subject to any disclaimer, the term of this patent is extended or adjusted under 35 U.S.C. 154(b) by 64 days.

(21) Appl. No.: 16/333,461

(22) PCT Filed: Sep. 12, 2017

(86) PCT No.: PCT/EP2017/072844
§ 371 (c)(1),
(2) Date: Mar. 14, 2019

(87) PCT Pub. No.: WO2018/054719
PCT Pub. Date: Mar. 29, 2018

(65) Prior Publication Data
US 2019/0255502 A1 Aug. 22, 2019

(30) Foreign Application Priority Data

Sep. 20, 2016 (WO) ................ PCT/CN2016/099465
Oct. 13, 2016 (EP) ..................................... 16193786

(51) Int. Cl.
| | | |
|---|---|---|
| *B01J 13/16* | (2006.01) |
| *C08K 3/36* | (2006.01) |
| *A61K 8/11* | (2006.01) |
| *A61Q 13/00* | (2006.01) |
| *A61Q 19/10* | (2006.01) |
| *C08G 18/08* | (2006.01) |
| *C08G 18/73* | (2006.01) |
| *C08G 18/76* | (2006.01) |
| *C08K 3/32* | (2006.01) |
| *C08K 3/34* | (2006.01) |
| *A61K 8/19* | (2006.01) |
| *A01N 25/28* | (2006.01) |
| *A61K 8/06* | (2006.01) |
| *C11D 3/50* | (2006.01) |
| *C11D 17/00* | (2006.01) |
| *C09K 23/00* | (2022.01) |

(52) U.S. Cl.
CPC .............. *B01J 13/16* (2013.01); *A01N 25/28* (2013.01); *A61K 8/06* (2013.01); *A61K 8/11* (2013.01); *A61K 8/19* (2013.01); *A61Q 13/00* (2013.01); *A61Q 19/10* (2013.01); *C08G 18/0876* (2013.01); *C08G 18/73* (2013.01); *C08G 18/76* (2013.01); *C08K 3/32* (2013.01); *C08K 3/346* (2013.01); *C08K 3/36* (2013.01); *A61K 2800/56* (2013.01); *C08K 2003/325* (2013.01); *C08K 2201/005* (2013.01); *C09K 23/002* (2022.01); *C11D 3/505* (2013.01); *C11D 17/0039* (2013.01)

(58) Field of Classification Search
CPC . A01N 25/28; A61K 8/06; A61K 8/11; A61K 8/19; A61K 2800/56; A61Q 13/00; A61Q 19/10; B01J 13/16; C08G 18/0876; C08G 18/73; C08G 18/76; C08K 3/32; C08K 3/346; C08K 3/36; C08K 2003/325; C08K 2201/005; B01F 17/0007; C11D 17/0039; C11D 3/50; C11D 3/505
See application file for complete search history.

(56) References Cited

U.S. PATENT DOCUMENTS

| | | | |
|---|---|---|---|
| 5,804,298 A | 9/1998 | Moy | |
| 6,204,900 B1 * | 3/2001 | Fergason | G02F 1/1334 349/86 |

FOREIGN PATENT DOCUMENTS

| | | |
|---|---|---|
| CN | 103394314 A | 11/2013 |
| WO | 96/33611 A2 | 10/1996 |
| WO | 2009/063257 A2 | 5/2009 |
| WO | 2011/154893 A1 | 12/2011 |
| WO | 2011/161618 A1 | 12/2011 |
| WO | 2013/182855 A2 | 12/2013 |
| WO | 2015/091705 A1 | 6/2015 |

OTHER PUBLICATIONS

International Search Report and Written Opinion, Appl. No. PCT/EP2017/072844, dated Nov. 8, 2017.
Li et al., "Pickering Emulsion Templated Layer-by-Layer Assembly for Making Microcapsules," Langmuir 2010, 26(19): 15554-15560.

* cited by examiner

*Primary Examiner* — Irina S Zemel
(74) *Attorney, Agent, or Firm* — Armstrong Teasdale LLP

(57) ABSTRACT

The present invention relates to a process for the preparation of formaldehyde-free organic-inorganic microcapsules, comprising a hydrophobic active ingredient-based core, preferably a perfume or a flavour, and a shell comprising inorganic particles consisting of non-chemically surface modified inorganic particles. Microcapsules obtained by said process are also an object of the invention. Consumer products comprising said capsules, in particular perfumed consumer products in the form of home care or personal care products, are also part of the invention.

8 Claims, 2 Drawing Sheets

HYBRID MICROCAPSULES

CROSS-REFERENCE

This application is a 371 filing of International Patent Application PCT/EP2017/072844, filed Sep. 12, 2017, which claims the benefit of International Patent Application PCT/CN2016/099465, filed Sep. 20, 2016, and European Patent Application 16193786.7, filed on Oct. 13, 2016.

TECHNICAL FIELD

The present invention relates to a process for the preparation of organic-inorganic microcapsules (also named hybrid microcapsules), with a hydrophobic active ingredient-based core, preferably a perfume or a flavour, and a polymeric shell comprising inorganic particles consisting of non-chemically surface modified inorganic particles. Microcapsules obtained by said process are also an object of the invention. Perfuming compositions and consumer products comprising said capsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. For instance, fragranced personal and household cleansers containing high levels of aggressive surfactant detergents are very challenging for the stability of microcapsules.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule walls, with chemical groups such as poly(amines) and poly(isocyanates), has been described as a way to improve stability of microcapsules. WO2011/154893 discloses for instance a process for the preparation of polyurea microcapsules using a combination of aromatic and aliphatic polyisocyanates in specific relative concentrations.

Stabilization of oil/water interfaces with inorganic particles has been described in so-called Pickering emulsions. In this context, functionalization of inorganic particles to allow their cross-linking is known. For instance, Pickering emulsions cross-linked from an outer water phase with polyelectrolytes providing electrostatic interactions have been the object of prior disclosures (Li Jian et al. in Langmuir (2010), 26(19), 15554-15560). However, such systems are very likely to dissociate in a surfactant base or in ethanol over time as electrostatic interactions are insufficient to promote stability. Covalent cross-linking has also been described in relation with Pickering emulsion in the preparation of colloidosomes. In particular, the use of diisocyanates as cross-linker has been disclosed in scientific publications. WO2009/063257 also describes the use of polyisocyanates as possible cross-linker for surface-modified inorganic particles in order to prepare microcapsules with increased level of protection from UV light for the contents. These products are typically intended for agrochemical applications. This type of system is not suitable for perfume encapsulation. In fact, in order to maintain a good morphology and permeability of the microcapsules, an excess of surface-modified inorganic particles is needed. Another problem is that these microcapsules show little margin for size adjustment. Furthermore, the amount of adsorbed particles at the oil-water interface is limited which affects the properties of the capsule membranes.

WO2015091705 discloses a process for the preparation of hybrid organic-inorganic microcapsules, also called "hybrid" microcapsules composed of at least two types of inorganic particles that are cross-linked. More specifically, this document discloses a first type of inorganic particles having at least one amine functionality and a second type of inorganic particles having at least one hydroxyl functionality.

The above cited prior art discloses stabilization of oil/water interfaces with chemically surface modified inorganic particles requiring therefore post chemical reaction and/or post chemical treatment to allow their cross-linking.

There is therefore a need to provide, in a simple and cost-effective way, stable microcapsules exhibiting good properties such as a high deposition onto surfaces, a low permeability with regard to the encapsulated active ingredient and a high blooming effect in terms of active ingredient delivery.

SUMMARY OF THE INVENTION

In a first aspect, the present invention relates to a process for the preparation of a formaldehyde-free organic-inorganic microcapsule slurry comprising the steps of:
1) suspending in water inorganic particles consisting of non-chemically surface modified inorganic particles to form a water phase;
2) admixing at least one polyisocyanate with a hydrophobic active ingredient-containing oil to form an oil phase;
3) adding the oil phase to the water phase and mixing them to form an oil-in-water Pickering emulsion under conditions allowing the formation of an inorganic-organic microcapsule slurry by interfacial polymerization, said process being characterized in that the water phase is essentially free from formaldehyde.

In a second aspect, the invention concerns a microcapsule slurry obtainable by such a process as well as perfuming compositions and consumer products containing them.

In a third aspect, the invention concerns a microcapsule powder obtainable by drying the microcapsule slurry as defined above as well as perfuming compositions and consumer products containing them.

In a last aspect, the invention relates to the use of inorganic particles consisting of non-chemically surface modified inorganic particles, for the stabilization of a Pickering emulsion further subjected to an interfacial polymerisation reaction.

DETAILED DESCRIPTION OF THE INVENTION

Unless stated otherwise, percentages (%) are meant to designate percent by weight of a composition.

Process for the Preparation of an Organic-Inorganic Microcapsule Slurry

A first object of the present invention consists of a process for the preparation of a formaldehyde-free organic-inorganic microcapsule slurry comprising the steps of:
1) suspending in water inorganic particles consisting of non-chemically surface modified inorganic particles to form a water phase;
2) admixing at least one polyisocyanate with a hydrophobic active ingredient-containing oil to form an oil phase;
3) adding the oil phase to the water phase and mixing them to form an oil-in-water Pickering emulsion under conditions allowing the formation of an inorganic-organic microcapsule slurry by interfacial polymerization,
said process being characterized in that the water phase is essentially free from formaldehyde.

By "essentially free from formaldehyde" it is meant that the water phase does not contain an amount of formaldehyde susceptible of further reacting with the polyisocyanate in a way that would substantially modify the nature of the capsule wall.

In other words, the raw materials used to produce the microcapsules do not contain a substantial amount of formaldehyde resins as for example melamine-formaldehyde resins.

According to an embodiment, the water phase is completely free from formaldehyde.

According to the invention, the process is devoid of any step consisting of adding chemically surface modified inorganic particles. In other words, only non-chemically surface modified inorganic particles are added in the process of the present invention.

The process of the invention comprises a step of forming a Pickering emulsion that is further subjected to interfacial reaction.

Without wishing to be bound by theory, it is believed that the Pickering emulsion determines the morphology and surface properties (size, density, zeta potential, stiffness) of the membrane, while the interfacial reaction determines the permeability and stiffness of the capsules.

Figure 1:
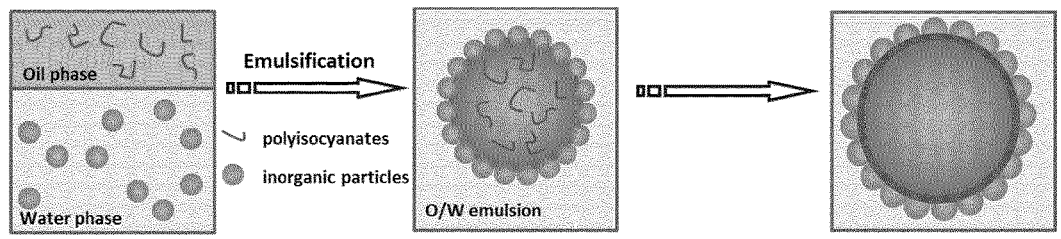
FIG. 1: is a schematic representation of the formation of a Pickering emulsion when non-chemically surface modified inorganic particles is used to stabilize the oil phase.

FIG. 1 schematises the formation of a Pickering emulsion when non-chemically surface modified inorganic particles are used. According to a particular embodiment, the microcapsules according to the invention are prepared in the absence of any molecular surfactant.

In the first step of the process, the non-chemically surface modified inorganic particles are dispersed in an aqueous phase with a pH preferably between 2 and 8. Typically, this is done using ultrasonic or high mechanical agitation. In a second step, at least one polyisocyanate is dissolved in a hydrophobic active ingredient-containing oil (for example, a perfume or flavour oil) to form an oil phase, which is then added to the water phase to form a Pickering emulsion, the mean droplet size of which is comprised between 1 and 3000 µm, preferably between 1 and 500 µm, more preferably between 5 and 50 microns. The oil-in-water Pickering emulsion is made for instance by using high speed mechanical disperser or ultrasonic dispersers at room temperature.

Once the Pickering emulsion is formed, the pH value is preferably adjusted to a value above 8.5 and preferably not higher than 11. However, this step can be omitted.

The interfacial reaction can be carried out typically at a temperature between 50° C. and 80° C. under stirring for 2 to 40 hours to complete the reaction and form inorganic-organic microcapsules in the form of a slurry.

The morphology of the microcapsules of the invention can vary from a core-shell to a matrix type. According to one embodiment, it is of the core-shell type. In this case, the microcapsules comprise a core based on a hydrophobic active ingredient, typically a perfume or flavour oil, and a shell comprising inorganic particles consisting of non-chemically surface modified inorganic particles.

Oil Phase

At least one polyisocyanate is dissolved in a hydrophobic active ingredient-containing oil to form an oil phase.

Polyisocyanates

Suitable polyisocyanates used according to the invention have at least two isocyanate functional groups and include aromatic polyisocyanate, aliphatic polyisocyanate and mixtures thereof.

According to a particular embodiment, the polyisocyanate comprises at least 3 but may comprise up to 6, or even only 4, isocyanate functional groups and the oil phase is essentially free from diisocyanate.

According to a particular embodiment, a triisocyanate (3 isocyanate functional groups) is used.

According to one embodiment, said polyisocyanate is an aromatic polyisocyanate. The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, said at least one polyisocyanate is in the form of a mixture of at least one aliphatic polyisocyanate and of at least one aromatic polyisocyanate, both comprising at least two isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

Preferably, the at least one polyisocyanate is hydrophobic.

Preferably, the at least one polyisocyanate is present in an amount comprised between 0.1wt % and 40 wt % of the oil phase, preferably from 0.5 to 15 wt %, even more preferably from 1 to 12 wt % of the oil phase.

According to a particular embodiment, the oil phase concentration is comprised between 5% and 60%, preferably between 20% and 40% of the Pickering emulsion.

Hydrophobic Active Ingredient

By "hydrophobic active ingredient", it is meant any active ingredient—single ingredient or a mixture of ingredients—which forms a two-phases dispersion when mixed with water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents present in the oil phase do not warrant a more detailed description here, which in any case would not be exhaustive, the skilled person being able to select them on the basis of its general knowledge and according to intended use or application.

Examples of such insect control agents are birch, DEET (N,N-diethyl-m-toluamide), essential oil of the lemon eucalyptus (*Corymbia citriodora*) and its active compound p-menthane-3,8-diol(PMD), icaridin (hydroxyethyl isobutyl piperidine carboxylate), Nepelactone, Citronella oil, Neem oil, Bog Myrtle (*Myrica gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to an embodiment, the hydrophobic active ingredient represents between 20 to 50% by weight relative to the total weight of the dispersion as obtained after step 3).

Aqueous Phase Particular Embodiments

According to a particular embodiment, the process of the invention comprises adding a polyamine or a polyol into the water phase during the reaction process. This additional step allows forming a more compact organic-inorganic shell. Examples of suitable polyamine include guanidine, guanidine salts, guanazole, ethylene diamine, 1,3-diaminopropane, hexamethylenediamine, putrescine, cadaverine, spermidine, spermine, polyallylamine, polyethyleneimine, polyetheramines and polyvinylamine. Examples of suitable polyol include ethylene glycol, glycerol, sucrose, pentaerythritol, polypropylene glycol, polytetrahydrofuran, diethylene glycol and polyethylene glycol.

According to a particular embodiment, no substantial amount of amine or polyamine or other water-soluble reactant susceptible to polymerize with the polyisocyanate such as polyols, thiols, ureas, urethanes, and mixtures thereof is added at any stage of the process.

According to another embodiment, the process further comprises a step of dispersing the microcapsule slurry in a solution of monomer or polymer selected from the group consisting of: amine, quaternary amines, dopamine, glycidyl ether, polyols, phenols, aminoacids, saccharide, hydrophilic isocyanate, and mixtures thereof.

According to another embodiment, the process comprises a further step consisting in adding a composition obtainable by reacting together:
1) a polyamine component in the form of melamine or of a mixture of melamine and at least one $C_{1-4}$ compound comprising two $NH_2$ functional groups;
2) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between about 1/1 and 10/1; and
3) a protic acid catalyst.
into the Pickeirng emulsion formed in step iii).

Such melamine-glyoxal resin is well-defined in WO2011161618 whose content is incorporated by reference.

Non-Chemically Surface Modified Inorganic Particles

By "non-chemically surface modified inorganic particles", it is meant that the surface of the particles has not been chemically modified so as to have reactive functional groups.

According to an embodiment, the inorganic particles defined in the present invention are not functionalized with an amino group.

Thus, according to the invention, no chemical treatment and/or modification have been carried on original particles.

In other words, the reactive functional group(s) of the inorganic particles according to the invention is (are) intrinsic properties of the particle.

The inorganic particles according to the invention can be synthetized or natural.

According to a particular embodiment, the non-chemically surface modified inorganic particles do not have an amine functional group such as $NH_2$.

According to an embodiment, the non-chemically surface modified inorganic particles are chosen in the group consisting of calcium phosphate, silica, silicates, titanium dioxide, aluminium oxide, zinc oxide, iron oxide, mica, kaolin, montmorillonite, laponite, bentonite, perlite, dolomite, diatomite, vermiculite, hectorite, gibbsite, illite, kaolinite, aluminosilicates, gypsum, bauxite, magnesite, talc, magnesium carbonate, calcium carbonate, diatomaceous earth and mixtures thereof.

According to an embodiment, calcium phosphate is chosen in the group consisting of hydroxyapatite, tricalcium phosphate and mixtures thereof.

According to an embodiment, the non-chemically surface modified inorganic particles are chosen from the group consisting of hydroxyapatite, tricalcium phosphate, kaolin, laponite, silica particles and mixtures thereof.

According to a particular embodiment, the non-chemically surface modified inorganic particles comprise, preferably consist of hydroxyapatite.

The microcapsules are thus defined as "organic-inorganic" or "hybrid" with reference to the nature of the shell that is composed of non-chemically surface modified inorganic particles to stabilize a Pickering emulsion and a polymeric shell formed from the interfacial polymerisation.

According to an embodiment, the non-chemically surface modified inorganic particles have a particle size comprised between 10nm and 20 µm, preferably between 100nm and 10 µm, more preferably between 200nm and 5 µm, even more preferably between 1 µm and 5 µm.

According to a particular embodiment, the non-chemically surface modified inorganic particles have a particle size greater than 30nm, preferably greater than 100nm.

By "particle size" it is meant an average diameter of particles based on size distribution measured by dynamic light scattering (DLS) using Zetasizer Nano ZS equipment from Malvern Instruments Ltd., UK when particles are dispersed into a water phase.

Preferably, the total amount of inorganic particles present in the aqueous phase is comprised between 0.1 and 20 wt %, preferably between 0.2 and 10 wt %.

Optional Step: Outer Coating

According to particular embodiment, the surface of the microcapsules obtained by the process of the invention can be modified with an additional step. Monomers or polymers suitable for surface modification are selected from compounds which can form chemical bond between the monomer or polymer and the microcapsules and which can improve the compatibility between the microcapsules and a target substrate.

Thus, according to a particular embodiment of the invention, during or at the end of step 3) of the process, one may also add to the invention's slurry a polymer selected from the group consisting of a non-ionic polysaccharide, a cationic polymer and mixtures thereof to form an outer coating to the microcapsule.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacryl ate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step 3). It is clearly understood by a person skilled in the art that only part of said added polymers will be incorporated into/deposited on the microcapsule shell.

Another object of the invention is a process for the preparation of a formaldehyde-free organic-inorganic microcapsule powder comprising the steps of:

1) suspending in water inorganic particles consisting of non-chemically surface modified inorganic particles to form a water phase;
2) admixing at least one polyisocyanate with a hydrophobic active ingredient-containing oil to form an oil phase;
3) adding the oil phase to the water phase and mixing them to form an oil-in-water Pickering emulsion under conditions allowing the formation of an inorganic-organic microcapsule slurry by interfacial polymerization,
4) drying the microcapsule slurry to obtain an organic-inorganic microcapsule powder said process being characterized in that the water phase is essentially free from formaldehyde.

Any drying method known to a skilled person in the art can be used; in particular the slurry may be spray-dried preferably in the presence of a polymeric carrier material such as polyvinyl acetate, polyvinyl alcohol, dextrines, natural or modified starch, vegetable gums, pectins, xanthanes, alginates, carragenans or cellulose derivatives to provide microcapsules in a powder form.

Microcapsule Slurry and Microcapsule Powder

A formaldehyde-free organic-inorganic microcapsule slurry and a formaldehyde-free organic-inorganic microcapsule powder obtainable by the above-described process are also an object of the invention.

According to an embodiment, the formaldehyde-free microcapsule slurry or the formaldehyde-free microcapsule powder includes at least one microcapsule comprising:

a) an oil-based core, preferably comprising a perfume;
b) a shell comprising inorganic particles consisting of non-chemically surface modified inorganic particles.

According to an embodiment, the non-chemically surface modified inorganic particles have a particle size comprised between 10nm and 20 µm, preferably between 100nm and 10 µm, more preferably between 200nm and 5 µm, even more preferably between 1 µm and 5 µm.

According to a particular embodiment, the non-chemically surface modified inorganic particles have a particle size greater than 30nm, preferably greater than 100nm.

Perfuming Composition

Another object of the present invention is a perfuming composition comprising:

(i) perfume microcapsule slurry or microcapsule powder as defined above, wherein the oil-based core comprises a perfume;
(ii) at least one ingredient selected from the group consisting of a perfumery carrier, a perfumery co-ingredient and mixtures thereof;
(iii) optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 30%, preferably between 0.1 and 30% by weight of microcapsules as defined above.

The invention's microcapsules can advantageously be used in many application fields and used in consumer products. Microcapsules can be used in liquid form applicable to liquid consumer products as well as in powder form, applicable to powdered consumer products.

Therefore, another object of the present invention is a liquid consumer product comprising:
a) from 2 to 65% by weight, relative to the total weight of the consumer product, of at least one surfactant;
b) water or a water-miscible hydrophilic organic solvent; and
c) microcapsule slurry as defined above,
d) optionally non-encapsulated perfume.

A powdered consumer product comprising
(a) from 2 to 65% by weight, relative to the total weight of the consumer product, of at least one surfactant;
(b) microcapsule powder as defined above.
(c) optionally perfume powder that is different from the microcapsules defined above is also an object according to the present invention.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also a powdered consumer product comprising:
(a) from 2 to 65% by weight, relative to the total weight of the consumer product, of at least one surfactant; and
(b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.), a hygiene product such as sanitary napkins, diapers, toilet paper.

According to a particular embodiment, the consumer product is selected from the group consisting of a shampoo, a shower gel, a rinse-off conditioner, a soap bar, a powder or a liquid detergent, a fabric softener and a floor cleaner.

According to a particular embodiment, the consumer product is a shampoo or a shower gel.

Preferably, the consumer product comprises from 0.05 wt %, preferably from 0.1 to 15wt %, more preferably between 0.2 and 5wt % of the microcapsules of the present invention, these percentages being defined by weight relative to the total weight of the consumer product. Of course the above concentrations may be adapted according to the olfactive effect desired in each product.

Another object of the invention is the use of inorganic particles consisting of non-chemically surface modified inorganic particles, for the stabilization of a Pickering emulsion further subjected to an interfacial polymerisation reaction.

The capsules of the invention have proven to be particularly and advantageously stable in consumer products containing significant amount of surfactant, while demonstrating good results in terms of deposition and blooming effect.

The invention will now be further described by way of examples. It will be appreciated that the invention as claimed is not intended to be limited in any way by these examples.

EXAMPLES

Example 1

Preparation of microcapsules comprising hydroxyapatite (HA) particles

Microcapsules A1

In the first step, a water phase is prepared from HA particles (Calcium hydroxyphosphate, from Aladdine Reagents (Shanghai) Co., LTD) dispersed in pH 4 buffer solution using ultrasonic probe. Then an oil phase including a polyisocyanate (Takenate® D-110N (74.4%) (trimethylol propane adduct of xylylene diisocyanate, trademark from: Mitsui Chemicals) is mixed with the aqueous phase. A Pickering emulsion is made by using a homogenizer, Ultra Turrax, IKA T25, at 24 000 rpm for 5 min. The formulation is described in Table 1 below.

TABLE 1

Formulation of microcapsules $A1_I$

| Ingredient | Mass/g |
|---|---|
| Hydroxyapatite[1] | 0.525 |
| pH 4 buffer[2] | 34.475 |
| Trimethylol propane-adduct of xylylene diisocyanate[3] | 0.6 |
| Perfume oil[4] | 14.4 |

[1] Calcium hydroxyphosphate, rod shaped with particle size of 4.2 μm, from Aladdine Reagents (Shanghai) Co., LTD
[2] CertiPUR® pH 4.00, from Merck KGaA.
[3] Takenate® D-110 N (74.4% solid content), trademark and origin from Mitsui
[4] see table 1a

TABLE 1a

Composition of the perfume
Table 1a) Composition of the perfume

| Ingredient | LogP | Amount [%] |
|---|---|---|
| Allyl (cyclohexyloxy)-acetate[a] | 2.72 | 1.2 |
| 2,4-Dimethyl-3-cyclohexene-1-carbaldehyde[b] | 2.85 | 1.2 |
| Menthone | 2.87 | 1.7 |
| Hedione®[c] | 2.98 | 5.8 |
| Camphor | 3.04 | 2.9 |
| Eucalyptol | 3.13 | 5.8 |
| Dihydromyrcenol[d] | 3.47 | 11.5 |
| Rose oxyde | 3.58 | 0.9 |
| Isobornyl acetate | 3.86 | 11.5 |
| Delta damascone | 4.13 | 0.6 |
| Cashmeran®[e] | 4.31 | 2.3 |
| Terpenyl acetate | 4.34 | 5.8 |
| Lilial®[f] | 4.36 | 17 |
| Linalyl acetate | 4.39 | 2.3 |
| Neobutenone® alpha[g] | 4.45 | 1.2 |
| Dihydromyrcenyl acetate | 4.47 | 2.3 |
| 2-Methylundecanal | 4.67 | 3.5 |
| Iso E Super®[h] | 4.71 | 11.5 |
| Cetalox®[i] | 4.76 | 0.6 |
| Isoraldeine® 70[j] | 4.84 | 2.3 |
| Habanolide®[k] | 4.88 | 4.6 |
| Precyclemone B[l] | 5.18 | 3.5 |
| Total | | 100.0 |

[a] Origin: Dragoco, Holzminden, Germany
[b] Origin: Firmenich SA, Geneva, Switzerland
[c] Methyl dihydrojasmonate, origin: Firmenich SA, Geneva, Switzerland
[d] Origin: International Flavors & Fragrances, USA

TABLE 1a-continued

Composition of the perfume
Table 1a) Composition of the perfume

| Ingredient | LogP | Amount [%] |
|---|---|---|

[e] 1,2,3,5,6,7-Hexahydro-1,2,3,3-pentamethyl-4h-inden-4-one, origin: International Flavors & Fragrances, USA
[f] 3-(4-Tert-butylphenyl)-2-methylpropanal, origin: Givaudan SA, Vernier, Switzerland
[g] 1-(5,5-Dimethyl-1-cyclohexen-1-yl)-4-penten-1-one, origin: Firmenich SA, Geneva, Switzerland
[h] 1-(Octahydro-2,3,8,8-tetramethyl-2-naphtalenyl)-1-ethanone, origin: International Flavors & Fragrances, USA
[i] Dodecahydro-3a,6,6,9a-tetramethyl-naphtho[2,1-b]furan, origin: Firmenich SA, Geneva, Switzerland
[j] 3-Methyl-4-(2,6,6-trimethyl-2cyclohexen-1-yl)-3-buten-2-one, origin: Givaudan SA, Vernier, Switzerland
[k] Pentadecenolide, origin: Firmenich SA, Geneva, Switzerland
[l] 1-Methyl-4-(4-methyl-3-pentenyl)cyclohex-3-ene-1-carboxaldehyde, origin: International Flavors & Fragrances, USA In the second step, interfacial reaction is carried out at 70° C. under stirring for 3 hours. The obtained microcapsules are in the form of a slurry (suspension in water).

Microcapsules $A1_{II}$ to $A1_{XII}$ were also prepared using the same protocol as described for A1 under various contents of hydroxyapatite particles and polyisocyanate concentration (see table 11 and table 13).

Microcapsules B1

In the first step, HA particles are dispersed in pH 4 buffer solution using ultrasonic probe to form a water phase. Then an oil phase comprising a mixture of two polyisocyanates is mixed with the aqueous phase. A Pickering emulsion is made by using an homogenizer, Ultra Turrax, IKA T25, at 24 000 rpm for 5 min. The formulation is described in Table 2 below.

TABLE 2

Formulation of microcapsules B1

| Ingredient | Mass/g |
|---|---|
| Hydroxyapatite[1] | 0.525 |
| pH 4 buffer[2] | 34.475 |
| Biuret of hexamethylene diisocynate[3] | 0.525 |
| Trimethylol propane-adduct of xylylene diisocyanate[4] | 0.32 |
| Perfume oil[5] | 14.045 |

[1] Calcium hydroxyphosphate, microsphere shaped with particle size of 5.0 μm, from Fluidinova, S.A.
[2] CertiPUR® pH 4.00, from Merck KGaA.
[3] Desmodur® N100 from Bayer
[4] Takenate® D-110N (74.4% solid content) from Mitsui
[5] see table 1a)

In the second step, interfacial reaction is carried out at 70° C. under stirring for 3 hours. The obtained microcapsules are in the form of a slurry (suspension in water).

Microcapsules C1

In the first step, a water phase is prepared from HA particles (Calcium hydroxyphosphate, from Fluidinova, S.A) dispersed in pH 4 buffer solution using ultrasonic probe. Then an oil phase including a polyisocyanate is mixed with the aqueous phase. A Pickering emulsion is made by using a homogenizer, Ultra Turrax, IKA T25, at 24 000 rpm for 5 min. The formulation is described in Table 3 below.

TABLE 3

Formulation of microcapsules C1$_I$

| Ingredient | Mass/g |
|---|---|
| Hydroxyapatite[1] | 0.35 |
| pH 4 buffer[2] | 34.65 |
| Trimethylol propane-adduct of xylylene diisocyanate[3] | 0.45 |
| Perfume oil[4] | 14.55 |

[1] Calcium hydroxyphosphate, microsphere shaped with particle size of 5.0 μm, from Fluidinova, S.A.
[2] CertiPUR ® pH 4.00, from Merck KGaA.
[3] Takenate ® D-110 N (74.4% solid content), trademark and origin from Mitsui
[4] see table 1a In the second step, interfacial reaction is carried out at 70° C. under stirring for 3 hours. The obtained microcapsules are in the form of a slurry (suspension in water). Microcapsules C1$_{II}$ were also prepared using the same protocol as described for C1 by using a different hydroxyapatite particles concentration (see table 11).

Example 2

Preparation of Microcapsules Comprising β-Tricalcium Phosphate (β-TCP) Particles Microcapsules A2

In the first step, a water phase is prepared from β-TCP particles dispersed in pH 4 buffer solution using ultrasonic probe. Then an oil phase including a polyisocyanate is mixed with the aqueous phase. A Pickering emulsion is made by using a homogenizer, Ultra Turrax, IKA T25, at 24 000 rpm for 5 min. The formulation is described in Table 4 below.

TABLE 4

Formulation of microcapsules A2$_I$

| Ingredient | Mass/g |
|---|---|
| β-Tricalcium phosphate[1] | 0.35 |
| pH 4 buffer[2] | 34.65 |
| Trimethylol propane-adduct of xylylene diisocyanate[3] | 0.45 |
| Perfume oil[4] | 14.55 |

[1] β-Tricalcium phosphate, with particle size of 4.0 μm, from Fluidinova, S.A
[2] CertiPUR ® pH 4.00, from Merck KGaA.
[3] Takenate ® D-110 N (74.4% solid content), trademark and origin from Mitsui
[4] see table 1a In the second step, interfacial reaction is carried out at 70° C. under stirring for 3 hours. The obtained microcapsules are in the form of a slurry (suspension in water). Microcapsules A2$_{II}$ were also prepared using the same protocol as described for A2 by using a different β-Tricalcium phosphate particles concentration (see table 11).

Example 3

Preparation of Microcapsules Comprising Pyrogenic Silica (Fumed Silica) Particles Microcapsules A3

In the first step, a water phase is prepared from fumed silica particles dispersed in pH 4 buffer solution using ultrasonic probe. Then an oil phase including a polyisocyanate is mixed with the aqueous phase. A Pickering emulsion is made by using a homogenizer, Ultra Turrax, IKA T25, at 24 000 rpm for 5 min. The formulation is described in Table 5 below.

TABLE 5

Formulation of microcapsules A3

| Ingredient | Mass/g |
|---|---|
| Fumed Silica[1] | 0.525 |
| pH 4 buffer[2] | 34.475 |
| Trimethylol propane-adduct of xylylene diisocyanate[3] | 0.45 |
| Perfume oil[4] | 14.55 |

[1] Fumed silica, with particle size of 3.6 μm, from Sigma-Aldrich
2) CertiPUR ® pH 4.00, from Merck KGaA.
[3] Takenate ® D-110 N (74.4% solid content), trademark and origin from Mitsui
[4] see table 1a In the second step, interfacial reaction is carried out at 70° C. under stirring for 3 hours. The obtained microcapsules are in the form of a slurry (suspension in water).

Example 4

Preparation of Microcapsules Comprising Kaolin Clay Particles

Microcapsules A4

In the first step, a water phase is prepared from kaolin clay particles dispersed in pH 4 buffer solution using ultrasonic probe. Then an oil phase including a polyisocyanate is mixed with the aqueous phase. A Pickering emulsion is made by using a homogenizer, Ultra Turrax, IKA T25, at 24 000 rpm for 5 min. The formulation is described in Table 6 below.

TABLE 6

Formulation of microcapsules A4

| Ingredient | Mass/g |
|---|---|
| Kaolinite clay[1] | 0.7 |
| pH 4 buffer[2] | 34.3 |
| Trimethylol propane-adduct of xylylene diisocyanate[3] | 0.45 |
| Perfume oil[4] | 14.55 |

[1] Kaolinite clay, with particle size of 0.6 μm, from Imerys S.A.
[2] CertiPUR ® pH 4.00, from Merck KGaA.
[3] Takenate ® D-110 N (74.4% solid content), trademark and origin from Mitsui
[4] see table 1a In the second step, interfacial reaction is carried out at 70° C. under stirring for 3 hours. The obtained microcapsules are in the form of a slurry (suspension in water).

Example 5

Preparation of Microcapsules Comprising Calcium Carbonate (CaCO$_3$) and β-Tricalcium Phosphate (β-TCP) Particles Microcapsules A5

In the first step, a water phase is prepared from Calcium carbonate and β-Tricalcium phosphate particles dispersed in Deionized water using ultrasonic probe. Then an oil phase including a polyisocyanate is mixed with the aqueous phase. A Pickering emulsion is made by using a homogenizer, Ultra Turrax, IKA T25, at 24 000 rpm for 5 min. The formulation is described in Table 7 below.

TABLE 7

Formulation of microcapsules A5

| Ingredient | Mass/g |
|---|---|
| Calcium carbonate[1] | 0.35 |
| β-Tricalcium phosphate[2] | |
| pH 4 buffer[3] | 34.65 |
| Trimethylol propane-adduct of xylylene diisocyanate[4] | 0.45 |
| Perfume oil[5] | 14.55 |

[1]Calcium carbonate, with particle size of 2.0 μm, from Boyu new materials Co., Ltd.
[2]β-Tricalcium phosphate, with particle size of 4.0 μm, from Fluidinova, S.A
[3]Deionized water
[4]Takenate ® D-110 N (74.4% solid content), trademark and origin from Mitsui
[5]see table 1a In the second step, interfacial reaction is carried out at 70° C. under stirring for 3 hours. The obtained microcapsules are in the form of a slurry (suspension in water).

Example 6 (Comparative)

Preparation of Non-Hybrid Microcapsules Comprising Polyvinyl Alcohol as Emulsifier Microcapsules X In the first step, PVOH 18-88 is dispersed in water. Then an oil phase comprising a polyisocyanate is mixed with the aqueous phase. An emulsion is made by using a homogenizer, Ultra Turrax, IKA T25, at 24 000 rpm for 3 min. The formulations are described in Table 8 (microcapsules X) and Table 9 (microcapsules Y) below.

TABLE 8

Formulation of comparative microcapsules X

| Ingredient | Mass/g |
|---|---|
| PVOH 18-88[1] | 0.265 |
| Water | 27.65 |
| Guanidine carbonate[2] | 0.45 |
| Trimethylol propane-adduct of xylylene diisocyanate[3] | 1.90 |
| Perfume oil[4] | 20.0 |

[1]Polyvinyl alcohol, Mowiol ® 18-88, from Sigma Aldrich
[2]Guanidine carbonate salt, from Sigma Aldrich
[3]Takenate ® D-110 N (74.4% solid content) from Mitsui
[4]see table 1a)

TABLE 9

Formulation of comparative microcapsules Y

| Ingredient | Mass/g |
|---|---|
| PVOH 18-88[1] | 0.29 |
| Water | 29.0 |
| Guanidine carbonate[2] | 0.11 |
| Trimethylol propane-adduct of xylylene diisocyanate[3] | 0.45 |
| Perfume oil[4] | 20.0 |

[1]Polyvinyl alcohol, Mowiol ® 18-88, from Sigma Aldrich
[2]Guanidine carbonate salt, from Sigma Aldrich
[3]Takenate ® D-110 N (74.4% solid content) from Mitsui
[4]see table 1a)

In the second step, interfacial reaction is carried out at 70° C. under stirring for 3 hours. The obtained microcapsules are in the form of a slurry (suspension in water).

Example 7 (Comparative)

Preparation of Hybrid Microcapsules Comprising Amino Functionalized $SiO_2$ Particles Microcapsule Z In the first step, a water phase is prepared from amino functionalized $SiO_2$ particles dispersed in pH 7 buffer solution using ultrasonic probe. Then an oil phase including a polyisocyanate is mixed with the aqueous phase. A Pickering emulsion is made by using a homogenizer, Ultra Turrax, IKA T25, at 24 000 rpm for 5 min. The formulation is described in Table 10 below

TABLE 10

Formulation of comparative microcapsules Z

| Ingredient | Mass/g |
|---|---|
| Amino-$SiO_2$ particles[1] | 0.525 |
| pH 7 buffer[2] | 34.475 |
| Trimethylol propane-adduct of xylylene diisocyanate[3] | 0.45 |
| Perfume oil[4] | 14.55 |

[1]Silicon Oxide Nanoparticles modified with amino group (product No. 6851HN), with particle size of 0.5 μm, from SkySpring Nanomaterials, Inc.
[2]CertiPUR ® pH 7.00, from Merck KGaA.
[3]Takenate ® D-110 N (74.4% solid content), trademark and origin from Mitsui
[4]see table 1a In the second step, interfacial reaction is carried out at 70° C. under stirring for 3 hours. The obtained microcapsules are in the form of a slurry (suspension in water).

Example 8

Storage Stability of Microcapsules in a Shower Gel Base

Composition of the Shower Gel Base

A predetermined amount of microcapsules slurry obtained by the process described in the previous examples was added into a shower gel under rapid stirring (1200 RPM for 10 min).

The shower gel contains 8.0% Polyacrylate-1 crosspolymer (Carbopol® Aqua CC polymer, origin: Noveon), 0.5% Citric acid (40% solution in water), 25.0% Sodium C12-C15 pareth sulfate (Zetesol AO 328 U, origin: Zschimmer & Schwarz), 4.0% Cocamidopropyl betaine (Tego Betain F 50, origin: Goldschmidt AG), 0.1% DMDM hydantoin and iodopropynyl butylcarbamate (Glydant Plus Liquid, origin: Lonza), 4.0% Sodium Chloride (20% solution in water) and 58.4% Water. The final encapsulated perfume oil content in the base was equal to 0.2%.

Stability Measurements

The shower gel base containing microcapsules was transferred into closed small bottles and kept at 45° C.

After 1 month storage at 45° C., 1.0 g of shower gel base containing the microcapsule slurry was mixed with 4.0 ml deionized water and extracted by 5.0 ml Isooctane/Diethyl ether with internal standard (75 mg/L Ethy Laurate in Isooctane/Diethyl ether). The extraction was shaken with IKA KS 130 basic at MOT 480/min for 15 min. Then the organic phase was filtered with 0.22 um RC membrane and analyzed by GC (7890A, Agilent Technologies)-MS (5975C, Agilent Technologies) to measure the leakage of perfume.

Results are shown in table 11.

TABLE 11

Stability measurements in a shower gel base (1 month—45° C.)

| Microcapsules | Concentration of particles in water % | Concentration of the oil phase % | Concentration of Polyisocyanate in oil % | Oil leakage % |
|---|---|---|---|---|
| X | 0 | 43% | 8.56% | 9.9% |
| Y | 0 | 41% | 2.23% | 91.3% |
| $A1_I$ | 1.5% (HA) | 30% | 2.98% | 7.4% |
| $A1_{II}$ | 1.5% (HA) | 30% | 3.72% | 7.1% |
| $A1_{III}$ | 1.5% (HA) | 30% | 5.73% | 5.7% |
| $A1_{IV}$ | 1.5% (HA) | 30% | 8.56% | 1.1% |
| $A1_V$ | 1.5% (HA) | 30% | 11.46% | 0% |
| $A1_{VI}$ | 0.5% (HA) | 30% | 5.73% | 2.1% |
| $A1_{VII}$ | 1.0% (HA) | 30% | 5.73% | 1.7% |
| $A1_{VIII}$ | 2.0% (HA) | 30% | 5.73% | 8.4% |
| $A1_{IX}$ | 3.0% (HA) | 30% | 5.73% | 7.9% |
| $A1_X$ | 1.5% (HA) | 30% | 2.23% | 8.6% |
| $C1_I$ | 1.0% (HA) | 30% | 2.23% | 11.8% |
| $C1_{II}$ | 1.5% (HA) | 30% | 2.23% | 12.4% |
| $A2_I$ | 1.0% (β-TCP) | 30% | 2.23% | 13.4% |
| $A2_{II}$ | 0.5% (β-TCP) | 30% | 2.23% | 15.9% |
| A5 | 0.75% ($CaCO_3$ + 0.75% β-TCP) | 30% | 2.23% | 4.5% |

The above results show that microcapsules prepared with microcapsules as defined in the present invention exhibit a lower oil leakage when compared with non-hybrid microcapsules when dispersed into shower gel base (1 month of storage at 45° C.).

Example 9

Deposition Performance of Microcapsules in a Shower Gel Base

A predetermined amount of microcapsules slurry obtained by the process described in the previous examples was added into a shower gel as disclosed in example 8 under rapid stirring (1200 RPM for 10 min).

Deposition Test

For the quantification of deposition, the following procedure was used. A 500 mg mini brown Caucasian hair swatch was wet with 40 mL of tap water (39° C.) aimed at the mount with a 140 mL syringe. The excess water was gently squeezed out once and 0.1 mL of a dilute shampoo base (shampoo base 1:1 diluted with water) containing microcapsules (with a dosage corresponding to 0.4% of perfume oil in dilute shampoo) loaded with a UV tracer (Uvinul A Plus) was applied with a 100 μL positive displacement pipet.

The shampoo base contains 0.4% of Guar Hydroxypropyltrimonium chloride (Jaguar C-14S, Rhone Poulenc), 7% of Coco-betaine (Dehyton AB-30, Cognis), 45% of Sodium Laureth Sulfate (Texapon NSO IS, Cognis), 3% of Dimethicone (and) Laureth-23 (and) Laureth-4 (and) Salicylic Acid (DOW CORNING 2-1691 EMULSION, Dow Corning), 0.9% of Glycol Distearate (CUTINA AGS, Cognis), 1.2% of Cocamide MIPA (REWOMID IPP 240, Degussa), 1.2% of Cetyl alcohol (Firmenich), 0.3% of DMDM Hydantoin (and) Iodopropynyl Butylcarbamate (GLYDANT PLUS LIQUID, Lonza), and 41.0% of deionized water.

The dilute shampoo was distributed with 10 horizontal and 10 vertical passes. The swatch was then rinsed with 100 mL of tap water (39° C.) with 50 mL applied to each side of the swatch aimed at the mount. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours. After the drying process, the vials were again weighed to determine the mass of the hair in the vials. Controls were also prepared by adding 0.1 mL of a model surfactant mixture containing microcapsules to an empty vial. 4 mL of 200 proof ethanol were then added to each vial and they were subjected to 60 min of sonication. After sonication, the samples were filtered through a 0.45 μm PTFE filter and analysed with a HPLC using a UV detector. To determine the percentage of deposition of microcapsules from a model surfactant mixture, the amount of Uvinul extracted from the hair samples was compared to the amount of Uvinul extracted from the control samples.

Results

TABLE 12

Deposition (%) performance of microcapsules in a shower gel base

| Microcapsules | Concentration of particles in water % | Concentration of the oil phase % | Concentration of Polyisocyanate in oil % | Deposition % |
|---|---|---|---|---|
| X | 0 | 43% | 8.56% | 2.6% |
| Y | 0 | 41% | 2.23% | 3.0% |
| Z | 1.5% ($NH_2$—$SiO_2$) | 30% | 2.23% | 32.3% |
| $A1_I$ | 1.5% (HA) | 30% | 2.98% | 33.7% |
| $A1_{II}$ | 1.5% (HA) | 30% | 3.72% | 42.6% |
| $A1_{III}$ | 1.5% (HA) | 30% | 5.73% | 36.9% |
| $A1_{IV}$ | 1.5% (HA) | 30% | 8.56% | 43.3% |
| $A1_V$ | 1.5% (HA) | 30% | 11.46% | 49.5% |
| $A1_{VI}$ | 2.0% (HA) | 30% | 5.73% | 34.1% |
| $A1_{IX}$ | 3.0% (HA) | 30% | 5.73% | 35.3% |
| $A1_X$ | 1.5% (HA) | 30% | 2.23% | 33.9% |
| $C1_I$ | 1.0% (HA) | 30% | 2.23% | 36.1% |
| $C1_{II}$ | 1.5% (HA) | 30% | 2.23% | 35.0% |
| $A2_{II}$ | 0.5% (β-TCP) | 30% | 2.23% | 33.0% |
| A4 | 2.0% (Kaolin) | 30% | 2.23% | 33.2% |

Conclusions

The above results underline that the deposition onto hair in a rinse-off application of hybrid microcapsules prepared with particles as defined in the present invention is significantly higher than the deposition obtained with non-hybrid microcapsules (microcapsules X and Y).

The above results also show that the deposition of hybrid microcapsules defined in the present invention (i.e comprising non-chemically modified inorganic particles) is higher than hybrid microcapsules comprising chemically modified inorganic particles (microcapsules Z).

Example 10

Olfactive Performance in a Shampoo Base

Experimental Part

A predetermined amount of microcapsule slurry obtained by the process described for preparing microcapsules A1 (prepared with various HA particles contents and polyisocyanate concentration—see compositions in the table 13) was dispersed into a shampoo base.

Figure 3:
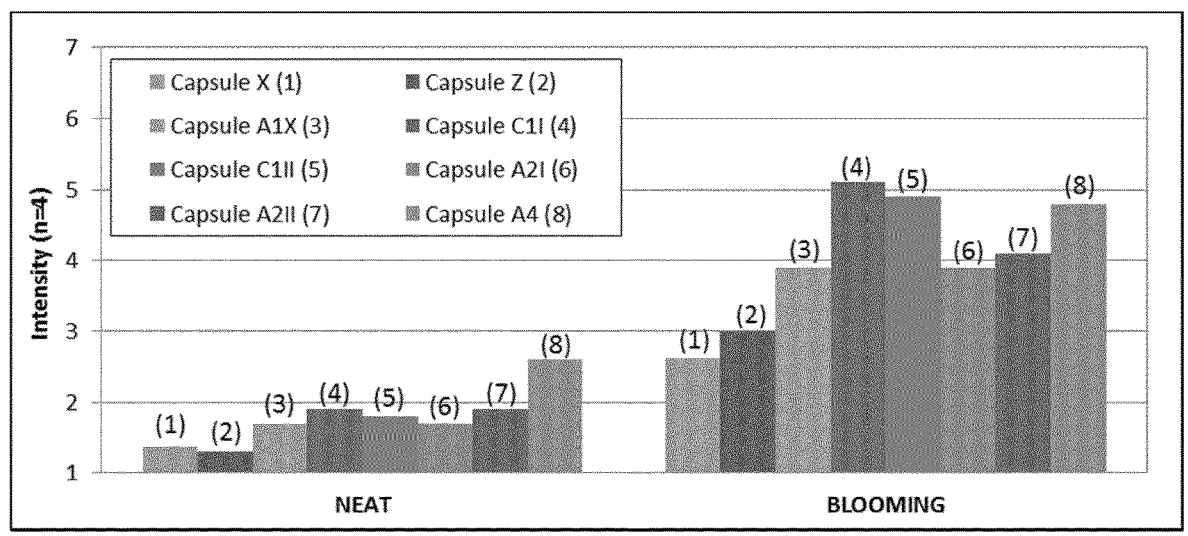

The same experiment was carried out for other microcapsules prepared by the process according to the invention (A1, A2, C1, A3 and A4 see FIG. 3).

TABLE 13

Microcapsules composition

| Microcapsules | Concentration of HA particles in water % | Concentration of Polyisocyanate in the oil phase % |
|---|---|---|
| X | 0 | 8.56% |
| A1$_{III}$ | 1.5 | 5.73% |
| A1$_{VII}$ | 1 | 5.73% |
| A1$_{VI}$ | 0.5 | 5.73% |
| A1$_{XI}$ | 1 | 2.23% |
| A1$_{XII}$ | 0.5 | 2.23% |

The shampoo base contains 0.05% of Tetrasodium EDTA (EDETA B POWDER, BASF), 0.2% of Hydroxyethylcellulose (TYLOSE H10 Y G4, SHIN ETSU), 0.1% of Polyquaternium-10 (UCARE POLYMER JR-400, Noveon), 23.2% of Ammonium Lauryl Sulfate (SULFETAL LA B-E, ZSHIMMER AND SCHWARZ), 0.8% of Laureth-2 (ARLYPON F, Cognis), 30% of Ammonium Laureth Sulfate (ZETESOL LA, Z&S HANDEL AG), 1.5% of Dimethicone (and) Laureth-23 (and) Laureth-4 (and) Salicylic Acid (DOW CORNING 2-1691 EMULSION, Dow Corning), 1.2% of cetyl alcohol (Firmenich), 1.5% of Cocamide MEA (COMPERLAN 100, COGNIS), 2% of Glycol Distearate (CUTINA AGS, Cognis), 0.1% of panthenol 75%, 0.4% of PHENOXYETHANOL (AND) PIROCTONE OLAMINE (NIPAGUARD PO 5, Clariant), and 38.95% of water deionized.

The final encapsulated perfume oil content in the base was equal to 0.2%.

4 to 6 expert panelists were selected for each evaluation. Samples of same quantity of shampoo were applied on hair swatches. The evaluation was made according to the following washing protocol:

(1) Hair swatch was first wetted by water, and then 1.5 ml surfactant mixture base was applied averagely along the hair.

(2) Hair was folded and rubbed 5 times in a circular movement with not too much pressure (3) The panelists evaluated the hair swatch after washing immediately.

Before washing, the panelists had to evaluate the intensity of the shampoo base as neat. Evaluation of Fragrance Intensity was done on a scale from 0 to 7, 0 meant no odor while 7 meant very strong.

Results

Figure 2:
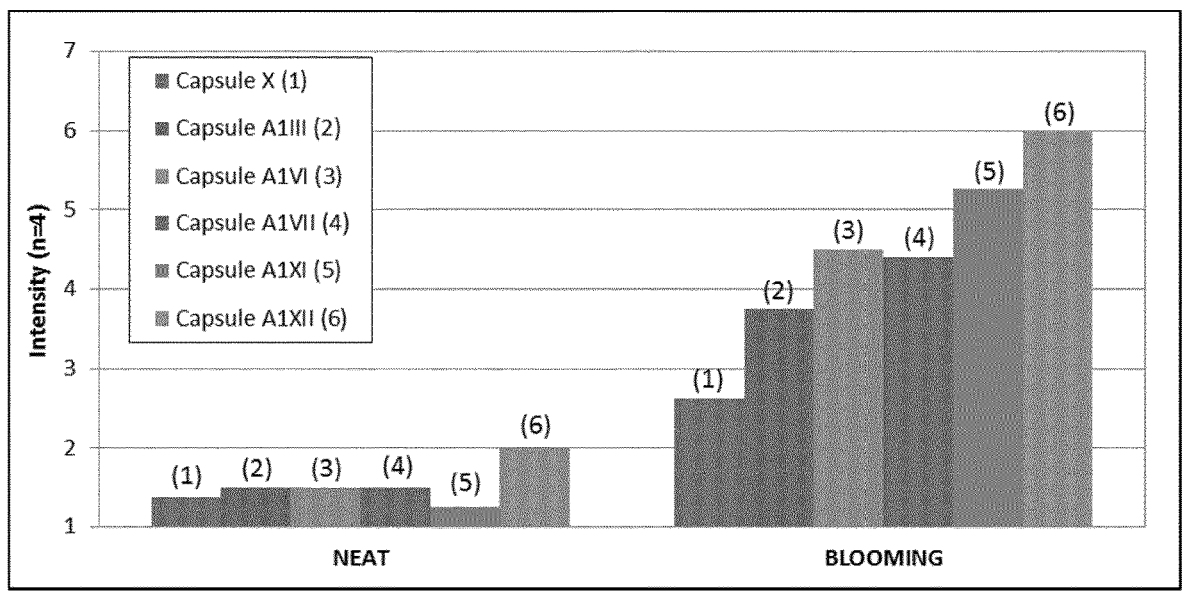
FIGS. 2 and 3 represent the perceived intensity of a perfume measured in a panel test comparing microcapsules according to the invention prepared with non-chemically surface modified particles versus comparative microcapsules (non-hybrid microcapsules (X) and hybrid microcapsules comprising chemically surface modified particles (Z)).

Results are shown in FIG. 2 and FIG. 3.

Conclusions

It can be concluded that microcapsules prepared with particles as defined in the present invention revealed strong intensity during washing, i.e. higher blooming effect compared to non-hybrid microcapsules and hybrid microcapsules comprising chemically-modified inorganic particles.

The present invention provides therefore cost-effective microcapsules (using only non-chemically modified inorganic particles) exhibiting good properties such as a high deposition onto surfaces, a low permeability with regard to the encapsulated active ingredient and a high blooming effect in terms of active ingredient delivery.

Example 11

Preparation of AP-Roll on Base Comprising Microcapsules of the Invention

A mixture of BRIJ 72 (3.25 g, Croda, UK), BRIJ721 (0.75 g, Croda, UK), and ARLAMOL E (4.00 g, Croda, UK), previously warmed up to 75° C., is to water (51.00 g) under stirring. The mixture is homogenised for 10 minutes and then cooled down to room temperature under stiring. LOCRON L (40.00 g, Clariant, Switzerland) is added slowly at 45° C., the mixture is kept at room temperature (see table 14).

Microcapsules slurry C1$_I$ (circa 2.60 g) is added at 35° C. to afford a white liquid emulsion with a concentration of encapsulated perfume oil of 1%, a neutral odor (pH 4.2-4.7) and with a viscosity between 1000 and 2500 cPs (measured 24 to 48 h after production).

TABLE 14

AP Roll on base composition

| Raw materials | Amount (g) | % (w/w) |
|---|---|---|
| BRIJ 72 | 3.25 | 3.17 |
| BRIJ 721 | 0.75 | 0.73 |
| ARLAMOL E | 4.00 | 3.90 |
| Water | 51.00 | 50.70 |
| LOCRON L | 40.00 | 39.00 |
| Capsule dispersion | 2.60 | 2.53 |
| TOTAL | 102.6 | 100 |

What is claimed is:

1. A process for the preparation of a formaldehyde-free organic-inorganic microcapsule slurry comprising the steps of:

1) suspending in water inorganic particles consisting of non-chemically surface modified inorganic particles to form a water phase;

2) admixing at least one polyisocyanate with a hydrophobic active ingredient-containing oil to form an oil phase; and
3) adding the oil phase to the water phase and mixing them to form an oil-in-water Pickering emulsion under conditions allowing the formation of an inorganic-organic microcapsule slurry by interfacial polymerization;
   wherein the water phase is essentially free from formaldehyde;
   wherein the non-chemically surface modified inorganic particles have a particle size greater than 100 nm;
   wherein the process does not comprise adding chemically surface modified inorganic particles;
   wherein no amine or polyamine is added at any stage of the process; and
   wherein no polyols, thiols, ureas, or urethanes are added at any stage of the process.

2. The process according to claim 1, wherein the non-chemically surface modified inorganic particles are selected in the group consisting of: calcium phosphate, silica, silicates, titanium dioxide, aluminium oxide, zinc oxide, iron oxide, mica, kaolin, montmorillonite, laponite, bentonite, perlite, dolomite, diatomite, vermiculite, hectorite, gibbsite, illite, kaolinite, aluminosilicates, gypsum, bauxite, magnesite, talc, magnesium carbonate, calcium carbonate, diatomaceous earth, and mixtures thereof.

3. The process according to claim 2, wherein the non-chemically surface modified inorganic particles comprise inorganic particles selected from the group consisting of: hydroxyapatite, tricalcium phosphate, kaolin, silica, laponite, and mixtures thereof.

4. The process according to claim 1, further comprising a step of dispersing the microcapsule slurry in a solution of monomer or polymer selected from the group consisting of: glycidyl ether, phenols, saccharide, hydrophilic isocyanate, and mixtures thereof.

5. The process according to claim 1, wherein the total amount of inorganic particles present in the water phase is between 0.1 and 20 wt % of the water phase.

6. The process according to claim 1, wherein the hydrophobic active ingredient is selected from the group consisting of: a perfume, flavor, nutraceuticals, cosmetics, insect control agents, biocide actives and mixtures thereof.

7. The process according to claim 6, wherein the hydrophobic active ingredient is selected from the group consisting of: a perfume and a flavour.

8. The process according to claim 1, wherein the total amount of inorganic particles present in the water phase is between 0.2 and 10 wt % of the water phase.

* * * * *